United States Patent [19]

Isshiki et al.

[11] 4,130,586

[45] Dec. 19, 1978

[54] PROCESS FOR PRODUCING IMINE COMPOUNDS

[75] Inventors: Tomiya Isshiki; Tetsuo Tomita; Mitsuo Abe, all of Tokyo; Norio Takeda, Matsudo, all of Japan

[73] Assignee: Mitsubishi Gas Chemical Company, Inc., Tokyo, Japan

[21] Appl. No.: 827,791

[22] Filed: Aug. 25, 1977

[30] Foreign Application Priority Data

Sep. 14, 1976 [JP] Japan .................................. 51-110448

[51] Int. Cl.² .......................................... C07C 119/00
[52] U.S. Cl. ................................................. 260/566 R
[58] Field of Search ..................................... 260/566 R

[56] References Cited

PUBLICATIONS

Smith, "The Chemistry of Open Chain Nitrogen Compounds," vol. 1, p. 329 (1965).

Arch. Pharm., vol. 243, p. 395 (1905).
Comp. Rend., vol. 169 (1919) p. 239.
Chem. Letter, vol. 1974, pp. 89, 1079.
Yuki Gosei Kagaku 33, No. 6 (1975), pp. 454–455.

*Primary Examiner*—Gerald A. Schwartz
*Attorney, Agent, or Firm*—Armstrong, Nikaido, Marmelstein & Kubovcik

[57] ABSTRACT

An imine compound is produced by reacting a benzophenone with ammonia in the presence of 0.01 to 10% by weight of a carboxylic acid as a catalyst at a reaction temperature of 50° to 350° C on the basis of benzophenone. Ammonia is fed to the reaction system continuously under a pressure of 2 to 15 atmospheres. A solvent may be used for the reaction. The catalyst carboxylic acid can be readily recovered and reused without any influence of water formed by the reaction and brings about no problem of corrosion to reactor apparatus.

8 Claims, No Drawings

PROCESS FOR PRODUCING IMINE COMPOUNDS

This invention relates to a process for producing imine compounds by reaction of benzophenones with ammonia, and more particularly to a process for producing diphenylmethaneimines in a liquid phase by condensation reaction of benzophenones with ammonia.

Processes for producing diphenylmethaneimines by reaction of benzophenones with ammonia are known. For example, there are disclosed a process comprising catalytic reaction in a gaseous phase of gaseous benzophenones with ammonia over a thorium oxide catalyst at a temperature of 390° C. (Compt. rend. 169 (1919), page 239), a process comprising saturating an ethanol solution of benzophenone with ammonia and heating the saturated solution at 150° to 180° C. in a liquid phase (Arch. Pharm. 243 (1905), page 395), and a process comprising adding zinc chloride and ammonium chloride to molten benzophenones and reacting the benzophenones with ammonia in a liquid phase at 200° C. (Chem. Lett. 1974, pages 89 and 1079). However, reaction of benzophenone with ammonia at a high temperature in a gaseous phase has such disadvantages that the raw material benzophenones undergo decomposition to by-produce nitriles, etc. Use of such salts as zinc chloride, aluminum chloride, etc. as the catalyst, or use of strong acids, as the catalyst has such problems that water formed by the reaction reacts with the catalyst to make the recovery or reuse of the catalyst difficult or that apparatuses are liable to be corroded. The reaction never proceeds without the catalyst at all.

The present inventors have made extensive studies of overcoming these disadvantages and problems, and have found a novel process having none of such disadvantages and problems.

The present invention provides a process for producing an imine compound represented by the general formula:

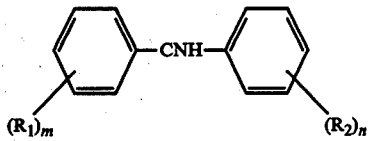

(I)

which comprises reacting a compound represented by the general formula:

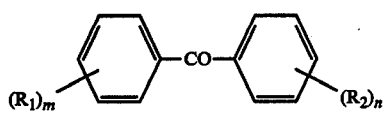

(II)

with ammonia in the presence of a carboxylic acid as a catalyst, wherein $R_1$ and $R_2$ represent hydrogen atoms, halogen atoms and alkyl, alkoxy and nitro group, and $R_1$ and $R_2$ may be the same or different from each other, and m and n are integers of 1 to 5.

Carboxylic acid used in the present invention as the catalyst includes aliphatic, alicyclic, aromatic and other carboxylic acids, for example, formic acid, acetic acid, propionic acid, butyric acid, isobutyric acid, valeric acid, pivalic acid, caproic acid, enanthic acid, caprylic acid, pelargonic acid, capric acid, undecanoic acid, lauric acid, dodecanoic acid, myristic acid, palmitic acid, stearic acid, chloracetic acid, bromacetic acid, fluoracetic acid, trichloracetic acid, trifluoracetic acid, glycollic acid, lactic acid, thioglycollic acid, acrylic acid, phenylacetic acid, α-naphthylacetic acid, oxalic acid, malonic acid, succinic acid, adipic acid, maleic acid, malic acid, citric acid, azelaic acid, phthalic acid, isophthalic acid, terephthalic acid, trimellitic acid, trimesic acid, nicotic acid, isonicotic acid, benzoic acid, tolylic acid, chlorobenzoic acid, nitrobenzoic acid, salicylic acid, anthranilic acid, lutidinic acid, glycine, alanine, methionine, leucine, etc. These carboxylic acids include those which are not in the form of carboxylic acid when added but can form carboxylic acids under the reaction conditions of the present invention, for example, they may be compounds capable of forming carboxylic acids in contact with water or by thermal decomposition. Examples of such compounds include ammonium carboxylates, acid amide nitriles, esters, acid chlorides, etc. They may be compounds capable of forming carboxylic acids by thermal decomposition at the reaction temperature.

The amount of carboxylic acid to be used in the present invention is not particularly limited, but generally 0.01 to 10% by weight, particularly 0.1 to 1% by weight of the carboxylic acid is preferable on the basis of the raw material benzophenone.

The reaction is carried out in a liquid phase in the present invention. The reaction temperature may be 50° to 350° C., preferably 150° to 250° C., and more particularly preferably about 200° C. The reaction pressure is not particularly limited, but an increased pressure under ammonia is preferable to enhance the conversion. That is, 1 to 50 atmospheres, particularly 2 to 15 atmospheres, is preferable. It is preferable to continuously feed ammonia in a gaseous phase to a reaction system to make it react with the benzophenones in the presence of said catalyst. Feed rate of ammonia per one mole of the benzophenones may be 0.1 to 100 Nl/min., preferably 0.5 to 10 Nl/min.

The reaction may be carried out in the presence of a solvent in the present invention. That is, when benzophenone is used as the raw material, it is sufficiently kept in a liquid state at the reaction temperature, because its melting point is 49° C. Since its liquid viscosity is also about 1 cp, a good ammonia dispersion can be obtained. Therefore, it is not always necessary to use a solvent, but an ammonia concentration in the reaction system can be increased, depending upon the kind of the solvent, and thus the use of a suitable solvent is effective for enhancing the reaction rate. Further advantage of using the solvent is that the benzophenone can be transferred in a liquid state at room temperature.

The solvent to be used in the present invention includes alcohols such as butanol, ethyleneglycol, and glycerine, amides such as benzamide, and dimethylformamide, and aromatic compounds such as toluene, xylene, pseudocumene, t-butylbenzene, and o-dichlorobenzene.

The benzophenones to be used as the raw material suitable for the present invention include 2-methylbenzophenone, 3-methylbenzophenone, 4-methylbenzophenone, 4-chlorobenzophenone, 4-nitrobenzophenone, 4-methoxybenzophenone, etc. beside benzophenone.

The carboxylic acid catalyst of the present invention has a good compatibility with the raw material benzophenones, and thus the amount of carboxylic acid to be added is not particularly limited. The carboxylic acid used as the catalyst can be readily recovered and reused without any influence by the water formed by the reaction, and also brings about no problem of corrosion of the reactor apparatus.

Now, the present invention will be explained in detail, referring to Examples, but will not be restricted to these Examples.

EXAMPLES 1-9

18.2 Grams of benzophenone was heated to 200° C. in a reactor together with a carboxylic acid shown in Table 1, and stirred while passing ammonia at a feed rate of 50 ml/min. under the atmospheric pressure. Two hours after the start of reaction, the reaction solution was cooled, and diluted with benzene, and benzophenoneimine was quantitatively determined by gas chromatographic analysis.

Table 1

| Ex. No. | Carboxylic acid | Amounts added Weight (g) | Moles | Benzophenone-imine yield (%) |
|---|---|---|---|---|
| 1 | Benzoic acid | 0.244 | 0.002 | 24 |
| 2 | p-Toluic acid | 0.272 | " | 26 |
| 3 | Nicotic acid | 0.246 | " | 29 |
| 4 | Isophthalic acid | 0.332 | " | 26 |
| 5 | Lutidinic acid | 0.334 | " | 29 |
| 6 | Trimesic acid | 0.420 | " | 18 |
| 7 | Caproic acid | 0.345 | " | 23 |
| 8 | α-Naphthylacetic acid | 0.373 | " | 30 |
| 9 | Azelaic acid | 0.345 | " | 30 |

EXAMPLES 10-12

Reaction was carried out in the same manner as in Examples 1-9, using benzoic acid as the catalyst except that the raw material benzophenones shown in Table 2 were used. The results are given in Table 2.

Table 2

| Ex. No. | Benzophenones Species | Amount used (g) | Benzoic acid Weight (g) | Moles | Benzo-phenone-imine yield (%) |
|---|---|---|---|---|---|
| 10 | 4-Methylbenzo-phenone | 19.6 | 0.244 | 0.002 | 27 |
| 11 | 4-tert.-Butyl-benzophenone | 23.8 | " | " | 16 |
| 12 | 4-Chlorobenzo-phenone | 21.7 | " | " | 24 |

EXAMPLE 13

91.1 Grams of benzophenone and 0.1 g of benzoic acid were charged into a pressure reactor, and an ammonia gas under 8 atmospheres was continuously fed to the reactor through a gas dispersing plate at a feed rate of 2 l/min. at a reaction temperature of 200° C. Reaction was carried out for 2 hours. As a result, benzophenoneimine was obtained in yield of 65%.

EXAMPLE 14

45.5 Grams of benzophenone, 50 ml of dimethylformamide and 0.1 g of benzoic acid were fed to a reactor. Ammonia gas was charged continuously at a feed rate of 0.5 l/min. (NTP) under 10 atmospheres at 155° C. of the reaction temperature for 1 hour. The yield of benzophenoneimine was 19%.

EXAMPLE 15

36.2 Grams of benzophenone, 50 ml of o-dichlorobenzene and 0.5 g of benzoic acid were fed to a reactor. Ammonia gas was passed through the reaction mixture under 6 atmospheres at 160° C. of the reaction temperature at a feed rate of 0.2 l/min. (NTP) continuously. The reaction was conducted for 3 hours and benzophenoneimine was obtained in yield of 26%.

What is claimed is:

1. A process for producing an imine compound represented by the general formula:

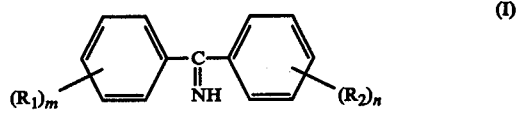
(I)

which comprises reacting, at a temperature of 50°-350° C., a compound represented by the general formula:

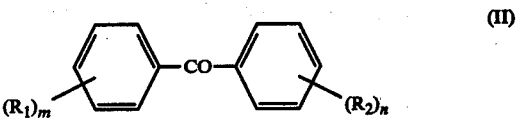
(II)

wherein $R_1$ and $R_2$ represent hydrogen atoms, halogen atoms and alkyl, alkoxy and nitro groups, and $R_1$ and $R_2$ may be the same or different from each other, and m and n are integers of 1 to 5, with ammonia at a pressure of 1-50 atmospheres in the presence of 0.01-10% by wt. based on compound II of a carboxylic acid from the group consisting of formic acid, acetic acid, propionic acid, butyric acid, isobutyric acid, valeric acid, pivalic acid, caproic acid, ethanic acid, caprylic acid, pelargonic acid, capric acid, undecanoic acid, lauric acid, dodecanoic acid, myristic acid, palmitic acid, stearic acid, chloracetic acid, bromacetic acid, fluoracetic acid, trichloracetic acid, trifluoracetic acid, glycollic acid, lactic acid, thioglycollic acid, acrylic acid, phenylacetic acid, α-naphthylacetic acid, oxalic acid, malonic acid, succinic acid, adipic acid, maleic acid, malic acid, citric acid, azelaic acid, phthalic acid, isophthalic acid, terephthalic acid, trimellitic acid, trimesic acid, nicotic acid, isonicotic acid, benzoic acid, tolylic acid, chlorobenzoic acid, nitrobenzoic acid, salicylic acid, anthranilic acid, lutidinic acid, glycine, alanine, methionine or leucine.

2. A process according to claim 1, wherein the reaction is carried out at 150° to 250° C.

3. A process according to claim 1, wherein the reaction is carried out in a liquid phase.

4. A process according to claim 1, wherein the carboxylic acid is an aliphatic, alicyclic, or aromatic carboxylic acid, or a compound capable of forming carboxylic acid.

5. A process according to claim 1, wherein the ammonia is continuously fed to reaction system.

6. A process according to claim 1, wherein reaction is carried out in the presence of a solvent.

7. A process according to claim 6, wherein the solvent is butanol, ethyleneglycol, glycerine, benzamide, dimethylformamide, toluene, xylene, pseudocumene, t-butylbenzene or o-dichlorobenzene.

8. A process according to claim 1, wherein the compound (II) is benzophenone, 2-methylbenzophenone, 3-methylbenzophenone, 4-methylbenzophenone, 4-chlorobenzophenone, 4-nitrobenzophenone or 4-methoxybenzophenone.

* * * * *